US011413502B2

(12) United States Patent
Zhang

(10) Patent No.: US 11,413,502 B2
(45) Date of Patent: Aug. 16, 2022

(54) ELECTRONIC DEVICE, METHOD FOR PUSHING INFORMATION, AND RELATED PRODUCTS

(71) Applicant: GUANGDONG OPPO MOBILE TELECOMMUNICATIONS CORP., LTD., Guangdong (CN)

(72) Inventor: Haiping Zhang, Guangdong (CN)

(73) Assignee: GUANGDONG OPPO MOBILE TELECOMMUNICATIONS CORP., LTD., Guangdong (CN)

( * ) Notice: Subject to any disclaimer, the term of this patent is extended or adjusted under 35 U.S.C. 154(b) by 335 days.

(21) Appl. No.: 16/584,930

(22) Filed: Sep. 26, 2019

(65) Prior Publication Data

US 2020/0164251 A1 May 28, 2020

(30) Foreign Application Priority Data

Nov. 26, 2018 (CN) .......................... 201811419639.8

(51) Int. Cl.
*G06F 3/048* (2013.01)
*A63B 24/00* (2006.01)
(Continued)

(52) U.S. Cl.
CPC ........ *A63B 24/0075* (2013.01); *A61B 5/0075* (2013.01); *A61B 5/145* (2013.01);
(Continued)

(58) Field of Classification Search
CPC ............ A63B 24/0075; A63B 24/0062; A63B 71/0622; G16H 20/30; A61B 5/0075; A61B 5/145; A61B 5/4866
See application file for complete search history.

(56) References Cited

U.S. PATENT DOCUMENTS 7,328,119 B1 * 2/2008 Pryor ..................... G06Q 30/06
702/127
9,289,674 B2 * 3/2016 Winsper ............ A63B 24/0075
(Continued)

FOREIGN PATENT DOCUMENTS

CN 102871664 1/2013
CN 103077299 5/2013
(Continued)

OTHER PUBLICATIONS

"Black technology in mobile phone for identifying substance composition of the first payment in the world," Jan. 2017, <http://www.360doc.com/content/17/0110/08/1751130_621454398.shtml>, 14 pages.
(Continued)

*Primary Examiner* — David Phantana-angkool
(74) *Attorney, Agent, or Firm* — Hodgson Russ LLP

(57) ABSTRACT

Provided are an electronic device, a method for pushing information, and related products. The method includes the following. A first set of data on multiple substances in a first position of a body of a user is obtained by scanning the first position with a substance detecting sensor. A body part corresponding to the first position is determined with a camera. Fitness plan is determined according to the first set of data and the body part and then pushed via a display.

18 Claims, 9 Drawing Sheets

(51) Int. Cl.
*G16H 20/30* (2018.01)
*A61B 5/00* (2006.01)
*A61B 5/145* (2006.01)
*A63B 71/06* (2006.01)

(52) U.S. Cl.
CPC .......... *A61B 5/4866* (2013.01); *A61B 5/6898* (2013.01); *A63B 24/0062* (2013.01); *A63B 71/0622* (2013.01); *G16H 20/30* (2018.01); *A61B 2562/063* (2013.01); *A63B 2220/803* (2013.01); *A63B 2230/06* (2013.01); *A63B 2230/207* (2013.01)

(56) References Cited

U.S. PATENT DOCUMENTS

| | | | | |
|---|---|---|---|---|
| 9,747,722 | B2* | 8/2017 | Adler | A63F 13/655 |
| 10,737,140 | B2* | 8/2020 | Rothman | A63B 24/0087 |
| 11,029,830 | B2* | 6/2021 | Otsuka | A45D 44/005 |
| 11,183,079 | B2* | 11/2021 | Rubinstein | G16H 40/67 |
| 11,316,941 | B1* | 4/2022 | Jain | H04L 67/535 |
| 2010/0190610 | A1* | 7/2010 | Pryor | G16H 20/60 482/8 |
| 2012/0277891 | A1* | 11/2012 | Aragones | A61B 5/02438 700/91 |
| 2017/0039336 | A1 | 2/2017 | Bitran et al. | |
| 2017/0263147 | A1* | 9/2017 | King | G11B 27/026 |
| 2017/0368413 | A1* | 12/2017 | Shavit | G06K 9/00342 |
| 2018/0036591 | A1* | 2/2018 | King | G09B 5/02 |
| 2020/0162451 | A1* | 5/2020 | Alhawaj | G06F 21/45 |
| 2021/0016149 | A1* | 1/2021 | Young | A63B 71/0616 |

FOREIGN PATENT DOCUMENTS

| | | |
|---|---|---|
| CN | 106137723 | 11/2016 |
| CN | 106821720 | 6/2017 |
| CN | 107239671 | 10/2017 |
| CN | 107506577 | 12/2017 |
| CN | 107657998 | 2/2018 |
| CN | 108090742 | 5/2018 |
| CN | 108417248 | 8/2018 |
| CN | 108472533 | 8/2018 |
| CN | 108766524 | 11/2018 |
| KR | 20160104520 | 9/2016 |
| KR | 101694393 | 1/2017 |

OTHER PUBLICATIONS

WIPO, English translation of the ISR and WO for PCT/CN2019/107345, dated Dec. 23, 2019.
IPI, Office Action for IN Application No. 201914039012, dated Jun. 28, 2021.
Consumer Physics, Inc., "Changhong H2, World's First Molecular Identification and Sensing Smartphone with a Miniaturized, Integrated Material Sensor, Unveiled at CES," Jan. 2017, retrieved from the internet: <:https://www.prnewswire.com/news-releases/changhong-h2-worlds-first-molecular-identification-and-sensing-smartphone-with-a-miniaturized-integrated-material-sensor-unveiled-at-ces-300385325.html>, 4 pages.
EPO, Office Action for EP Application No. 19200127.9, dated Apr. 1, 2020.
SIPO, First Office Action for CN Application No. 201811419639.8, dated Mar. 25, 2021.
CNIPA, Office Action issued in CN Application No. 201811419639.8, dated Jan. 26, 2022.
EPO, Communication Pursuant to Article 94(3) EPC issued in European Application No. 19200127.9, dated Feb. 28, 2022.

* cited by examiner

ELECTRONIC DEVICE, METHOD FOR PUSHING INFORMATION, AND RELATED PRODUCTS

CROSS-REFERENCE TO RELATED APPLICATION(S)

This application claims priority to Chinese Patent Application No. 2018114196398, filed on Nov. 26, 2018, the entire disclosure of which is incorporated herein by reference.

TECHNICAL FIELD

This disclosure relates to the field of electronic technology, and more particularly to an electronic device, a method for pushing information, and related products.

BACKGROUND

With wide popularity of mobile terminals (such as smart phones), the mobile terminal can support an increasing number of applications and is becoming more powerful. The smart phone is becoming more diversified and personalized and has become an indispensable electronic product in users' life.

Currently, people often do gyms. However, fitness exercise will be ineffective if it is done without guidance. In addition, although some fitness devices can monitor a heart rate of a user and the like, these fitness devices are unable to efficiently guide the user in fitness activities in the absence of manual intervention.

SUMMARY

In a first aspect of the present disclosure, an electronic device is provided. The electronic device includes a processor, a substance detecting sensor, a camera, and a display. The substance detecting sensor, the camera, and the display are respectively coupled with the processor. The substance detecting sensor is configured to obtain a first set of data on multiple substances in a first position of a body of a user by scanning the first position. The camera is configured to determine a body part corresponding to the first position. The processor is configured to determine a fitness plan according to the first set of data and the body part and push the fitness plan via the display.

In a second aspect of the present disclosure, a method for pushing information is provided. The method is applicable to an electronic device including a substance detecting sensor, a camera, and a display. The substance detecting sensor is disposed near the camera. The method includes the following. A first set of data on multiple substances in a first position of a body of a user is obtained by scanning the first position with the substance detecting sensor. A body part corresponding to the first position is determined with the camera. A fitness plan is determined according to the first set of data and the body part and then pushed via the display.

In a third aspect of the present disclosure, a computer readable storage medium is provided. The computer readable storage medium is configured to store computer programs which, when executed by a computer, are operable with the computer to: invoke a sensor to scan a first position of a body of a user to obtain a first set of data on a plurality of body substances in the first position, wherein the first set of data comprises at least one of: contents of each body substance, and percentage of each body substance; invoke a camera to capture a picture of the first position; invoke a processor to determine a body part corresponding to the first position by feature analysis of the picture; invoke the processor to determine a fitness plan according to the first set of data and the body part and push, via the display, the fitness plan determined.

BRIEF DESCRIPTION OF THE DRAWINGS

In order to describe technical solutions of implementations of the present disclosure or the related art more clearly, the following will give a brief description of accompanying drawings used for describing implementations of the present disclosure or the related art. Apparently, accompanying drawings described below are merely some implementations of the present disclosure. Those of ordinary skill in the art can also obtain other accompanying drawings based on the accompanying drawings described below without creative efforts.

DETAILED DESCRIPTION

In order for those skilled in the art to better understand technical solutions of the present disclosure, technical solutions of implementations of the present disclosure will be described clearly and completely with reference to accompanying drawings in implementations of the present disclosure. Apparently, implementations described hereinafter are merely some implementations, rather than all implementations, of the present disclosure. All other implementations obtained by those of ordinary skill in the art based on implementations of the present disclosure without creative efforts shall fall within the protection scope of the present disclosure.

The terms "first", "second", and the like used in the specification, the claims, and the accompany drawings of the present disclosure are used to distinguish different objects rather than describe a particular order. The terms "include", "comprise", and "have" as well as variations thereof are intended to cover non-exclusive inclusion. For example, a process, method, system, product, or apparatus including a series of steps or units is not limited to the listed steps or units. Instead, it can optionally include other steps or units that are not listed; alternatively, other steps or units inherent to the process, method, product, or apparatus can also be included.

The term "implementation" referred to herein means that a particular feature, structure, or character described in conjunction with the implementation may be contained in at least one implementation of the present disclosure. The phrase appearing in various places in the specification does not necessarily refer to the same implementation, nor does it refer to an independent or alternative implementation that is mutually exclusive with other implementations. It is explicitly and implicitly understood by those skilled in the art that an implementation described herein may be combined with other implementations.

An electronic device in implementations of the disclosure may include various handheld devices, in-vehicle devices, wearable devices, computing devices that have wireless communication functions or other processing devices connected to the wireless modem, as well as various forms of user equipment (UE), mobile stations (MS), terminal devices, and the like. For the convenience of description, the above-mentioned devices are collectively referred to as the electronic device.

Hereinafter, implementations of the disclosure will be described in detail.

Figure 1A:
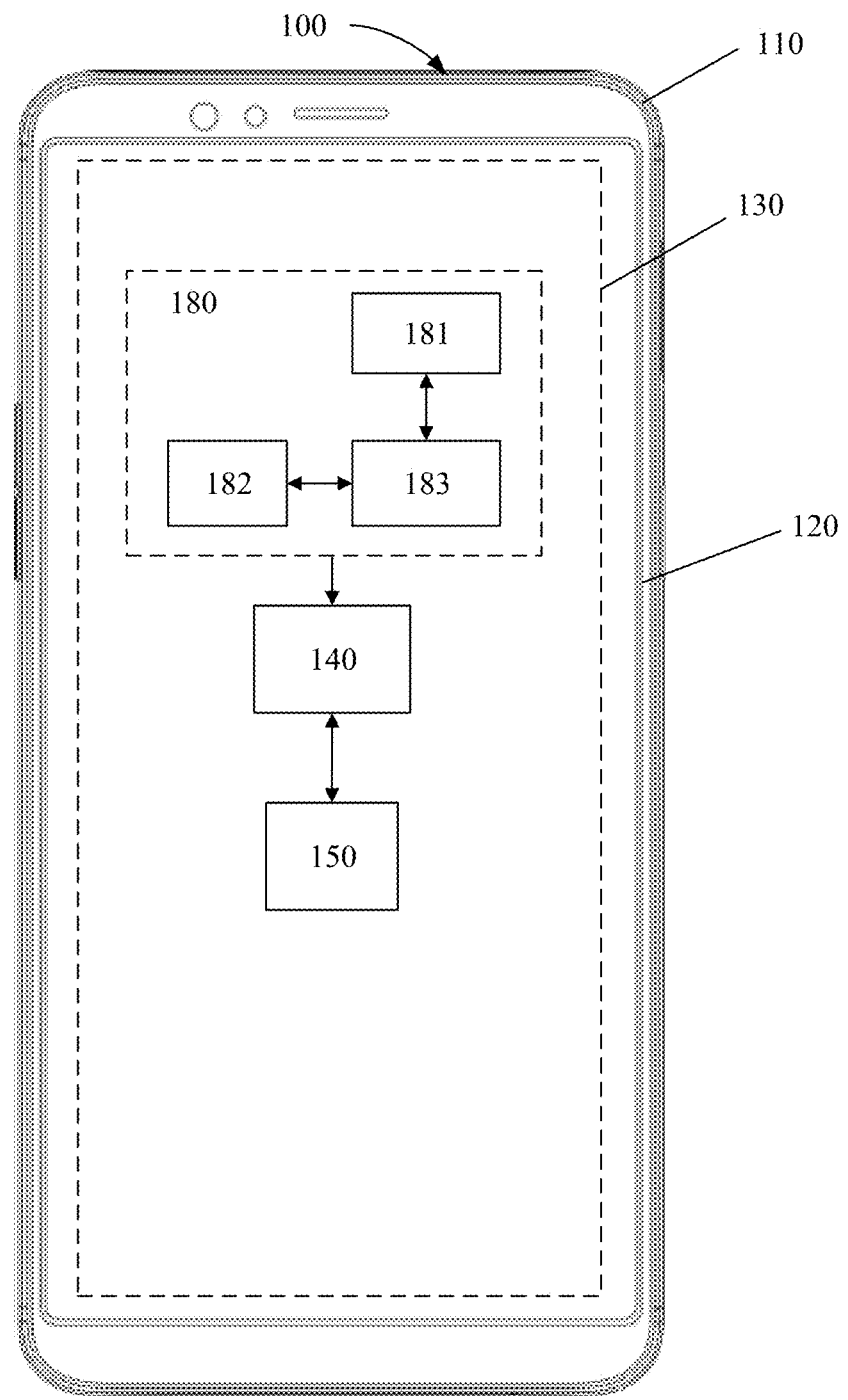
FIG. 1A is a schematic structural diagram of an electronic device according to an implementation of the present disclosure.
Figure 1B:
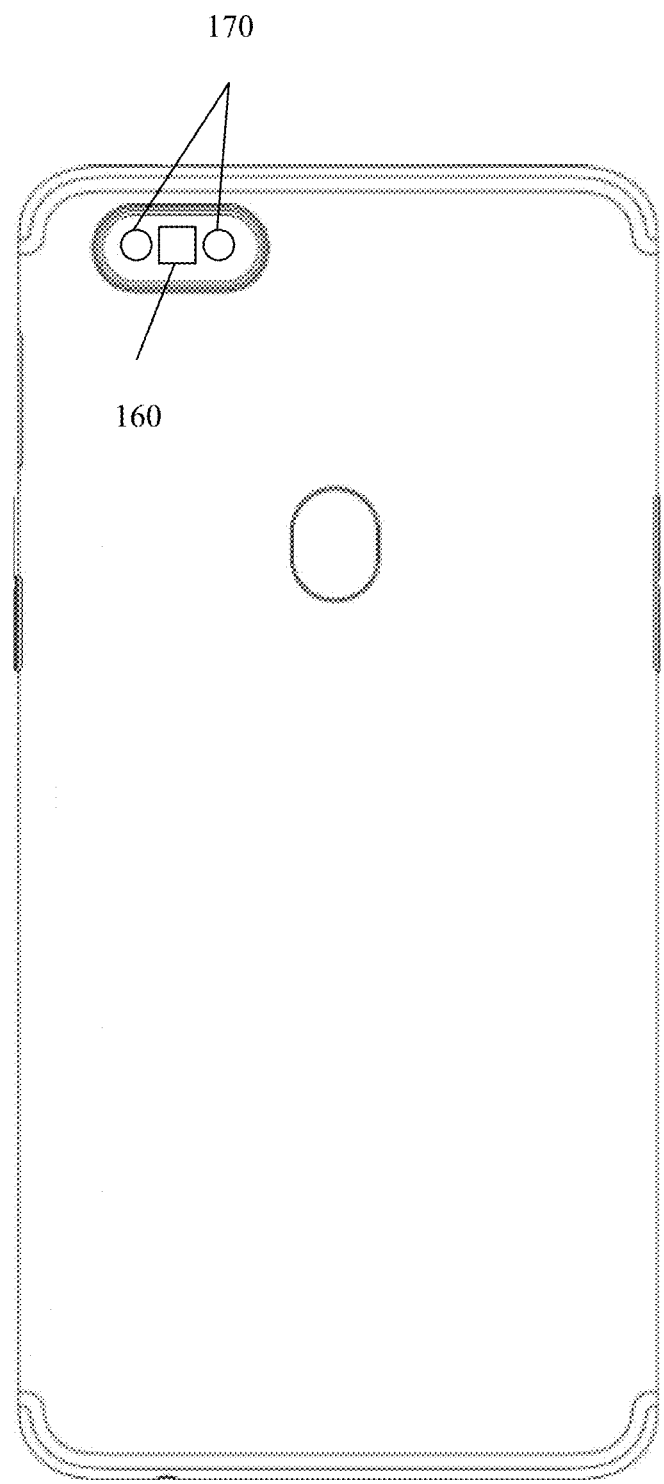
FIG. 1B is a schematic diagram of a positional relationship between a substance detecting sensor and a camera according to an implementation of the present disclosure.

FIG. 1A is a schematic structural diagram of an electronic device 100 according to an implementation of the present disclosure. As illustrated in FIG. 1A, the electronic device 100 includes a casing 110, a display 120 disposed on the casing 110, and a mainboard 130 disposed inside the casing 110. The mainboard 130 is provided with a processor 140 and a memory 150. As illustrated in FIG. 1B, the electronic device is further provided with a substance detecting sensor 160, a camera 170, etc. The substance detecting sensor 160 and the camera 170 are coupled with the processor 140. The processor 140 is coupled via the display 120. The electronic device 100 further includes a radio frequency system 180 illustrated in FIG. 1A. The radio frequency system 180 includes a transmitter 181, a receiver 182, and a signal processor 183.

The substance detecting sensor 160 is configured to obtain a first set of data on multiple substances in a first position of a body of a user by scanning the first position. The camera 170 is configured to determine a body part corresponding to the first position. The processor 140 is configured to determine at least one fitness plan according to the first set of data and the body part and push, via the display 120, the fitness plan determined.

The display 120 includes a display driver circuit, a display screen, and a touch screen. The display driver circuit is configured to control the display screen to display contents according to display data and display parameters (such as brightness, color, and saturation) of a picture. The touch screen is configured to detect touch operations. The display screen is an organic light emitting diode (OLED) display.

Figure 1C:
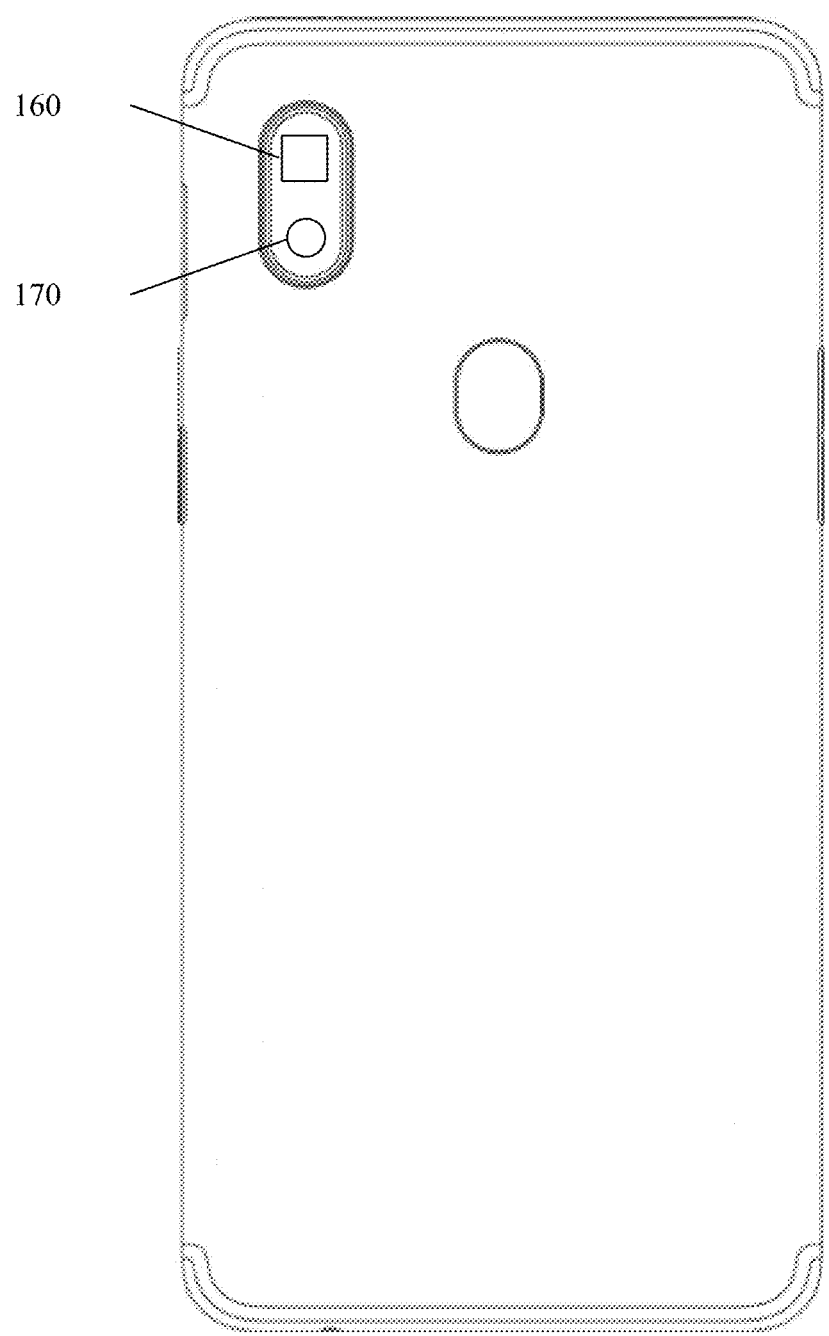
FIG. 1C is a schematic diagram of a positional relationship between a substance detecting sensor and a camera according to another implementation of the present disclosure.

The camera 170 can be a front-facing camera or a rear-facing camera of the electronic device 100. However, no matter whether the camera 170 is the front-facing camera or the rear-facing camera, the substance detecting sensor 160 is disposed near the camera 170. For example, as illustrated in FIG. 1B, the camera 170 is implemented as dual rear-facing cameras, and the substance detecting sensor 160 is located between the double back cameras. Alternatively, as illustrated in FIG. 1C, the camera 170 is implemented as a single rear-facing camera, and the substance detecting sensor 160 is disposed directly above the single back camera, which is not particularly limited herein.

The substance detecting sensor 160 can detect multiple substances, such as water, sugar, blood oxygen, fat, and the like. Since different substances have different absorbing capacities to an infrared spectrum, the substance detecting sensor 160 can be integrated with multiple channels. During substance detection, an infrared light emitting diode (LED) lamp of the substance detecting sensor 160 emits infrared lights. Then a light acquisition device of the substance detecting sensor 160 collects infrared lights of different wavelengths from each of the multiple channels, these infrared lights are of different wavelengths because they are reflected back after being projected onto different substances. The light acquisition device then sends data on infrared lights collected to the processor 140, such that the processor 140 can draw an infrared spectrum and conduct a big data analysis on the infrared spectrum to determine the composition of a substance.

The mainboard 130 can be in any size and shape that can be accommodated by the electronic device 100, which is not specifically limited herein.

The processor 140 includes an application processor and a baseband processor. The processor 140 is a control center of the electronic device 100. The processor 140 is configured to connect various parts of the entire electronic device through various interfaces and lines, and to execute various functions of the electronic device 100 and process data by running or executing software programs and/or modules stored in the memory 150 and invoking data stored in the memory 150, thereby monitoring the electronic device 100 as a whole. The application processor is mainly configured to handle and maintain an operating system, a user interface, applications, and so on. The baseband processor is mainly configured to process wireless communication. It will be appreciated that the baseband processor mentioned above may not be integrated into the processor 140.

The memory 150 is configured to store software programs and modules. The processor 140 is configured to execute various function applications and data processing of the electronic device 100 by running the software programs and the modules stored in the memory 150. The memory 150 mainly includes a program storage area and a data storage area. The program storage area may store an operating system, applications required for at least one function, and so on. The data storage area may store data created according to use of the electronic device, and so on. In addition, the memory 150 may include a high-speed random access memory (RAM), and may further include a non-volatile memory such as at least one disk storage device, a flash device, or other non-volatile solid storage devices.

As can be seen, in this implementation, the electronic device obtains the first set of data on the multiple substances in the first position of the body of the user by scanning the first position with the substance detecting sensor; determines, with the camera, the body part corresponding to the first position; pushes the fitness plan according to the first set of data and the body part. As such, the electronic device can determine, with the camera and the substance detecting sensor respectively, a substance content of any part of the body of the user, such that more convenient and accurate substance detection for human body can be achieved. In addition, an effective fitness plan can be designed for a specific body part according to substance composition detected, which is possible to achieve an accurate fitness guidance for the user to avoid indiscriminate fitness exercise and thus beneficial to achieving convenient and proper fitness exercise for the user.

In some implementations, in terms of pushing, via the display, the fitness plan according to the first set of data and the body part, the processor 140 is configured to: for each data in the first set of data, determine a numerical interval to which the data, and assign a score to the data according to the numerical interval; calculate a total score of the first set of data according to a weight of each data in the first set of data; determines a fitness plan which matches the total score and the body part as the fitness plan to be pushed; push, via the display, the fitness plan.

In some implementations, in terms of acquiring the fitness plan which matches the total score and the body part, the processor 140 is configured to: acquire a target score which is set in advance, for example by the user; receive, from a database, fitness plans which match the body part, where for each of the fitness plans received from the database, a difference between a score before a reference user carries out the fitness plan and the total score is smaller than a first threshold, and a difference between a score after the reference user carries out the fitness plan and the target score is smaller than a second threshold. The "reference user" here refers to a user different from the user to whom the fitness plan is pushed.

In some implementations, after receiving, from the database, the fitness plans which match the body part, the processor 140 is further configured to: select, from the fitness plans, at least one fitness plan which matches identity information of the user.

In some implementations, the fitness plan includes an exercise plan. After pushing, via the display, the fitness plan according to the first set of data and the body part, the processor 140 is further configured to: when the exercise plan is carried out by the user, acquire a heart rate and a blood oxygen level of the user; guide the user in exercise velocity according to the heart rate and the blood oxygen level.

In some implementations, the electronic device 100 further includes a velocity sensor 191. In terms of guiding the user in exercise velocity according to the heart rate and the blood oxygen level, the processor 140 is configured to: acquire, with the velocity sensor 191, a first exercise velocity of the user; determine, according to the first exercise velocity, a first standard interval for the heart rate and a second standard interval for the blood oxygen level; output a reminder message via the display 120, when the heart rate is higher than a maximum value of the first standard interval and/or the blood oxygen level is lower than a minimum value of the second standard interval, where the reminder message is used for reminding the user to reduce the first exercise velocity to a second exercise velocity.

In some implementations, the fitness plan further includes a diet plan. After pushing, via the display, the fitness plan according to the first set of data and the body part, the substance detecting sensor 160 is further configured to: when the diet plan is carried out by the user, acquire a second set of data on food by scanning the food. The processor 140 is further configured to guide the user in carrying out the diet plan according to the second set of data.

In some implementations, in terms of guiding the user in carrying out the diet plan according to the second set of data, the substance detecting sensor 160 is configured to: determine a total amount of the food by scanning the food. The processor 140 is configured to determine a first calorie value in the second set of data and determine a second calorie value in the diet plan, compare the first calorie value with the second calorie value, and guide the user in carrying out the diet plan by pushing an intake of the food according to the second calorie value in the diet plan, the total amount of the food, and the first calorie value in the second set of data, when the first calorie is detected to be higher than the second calorie.

Optionally, the total amount of the food can also be determine by taking a picture of the food via the camera and then analyzing the picture. Still optionally, the first calorie value in the second set of data can also be determined at the substance detecting sensor 160 rather than the camera. In short, data analysis function used herein can be integrated into the sensor, the processor, or even the camera, which is not limited.

Figure 2A:
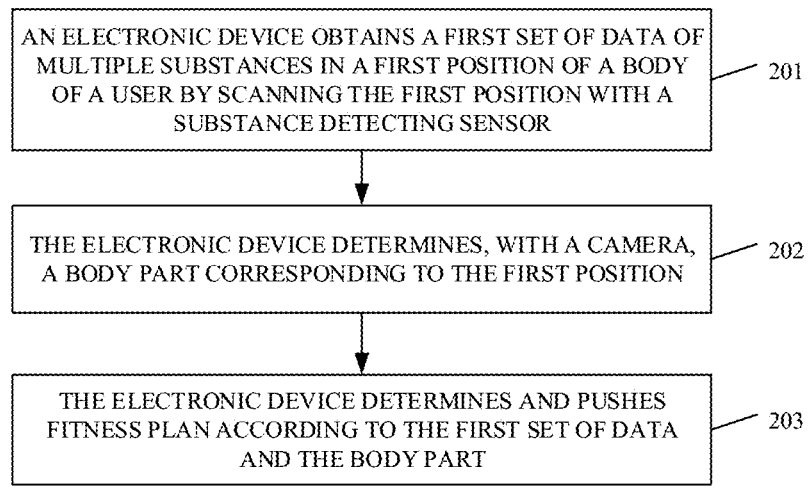
FIG. 2A is a schematic flowchart of a method for pushing information according to an implementation of the present disclosure.

FIG. 2A is a schematic flowchart of a method for pushing information according to an implementation of the present disclosure. The method is applicable to the electronic device illustrated in FIG. 1A to FIG. 1C. The electronic device includes a substance detecting sensor, a camera, and a camera. The substance detecting sensor is disposed near the camera. In the method, the electronic device first obtains a first set of data on multiple substances in a first position of a body of a user by scanning the first position with the substance detecting sensor, then determines a body part corresponding to the first position, for example with the camera, and determines a fitness plan according to the first set of data and the body part and then pushes the fitness plan determined via the display. As illustrated in FIG. 2A, the method begins at block 201.

At 201, the electronic device obtains a first set of data on multiple substances in a first position of a body of a user by scanning the first position with the substance detecting sensor.

Figure 2B:
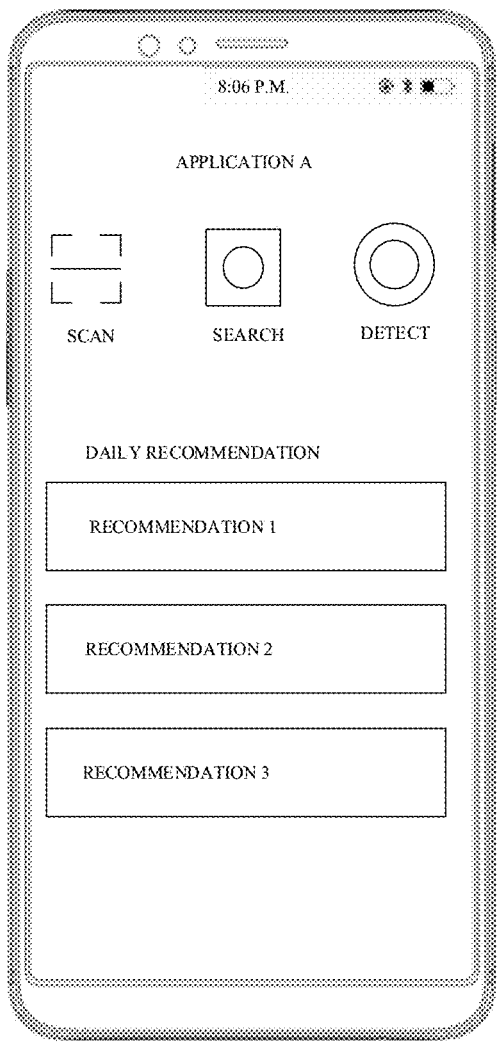
FIG. 2B is an exemplary diagram of a display interface of a fitness application according to an implementation of the present disclosure.

The electronic device can be provided with a fitness guiding application (APP). An interface of the fitness guiding application is illustrated in FIG. 2B. A scanning function can be enabled by clicking a scanning icon or a scanning function key of the fitness guiding application, that is, the substance detecting sensor of the electronic device is enabled to scan the first position that can be scanned currently, to obtain the first set of data on the multiple substances. The fitness guiding application may further include a query icon for the user to query the fat content, the water content, etc. of different foods, or may further include a test icon to test user's constitution, or may further include multiple recommended exercise schemes, multiple recommended diet schemes, etc., which is not limited herein.

The first position may be any part of the body, such as the arm, the abdomen, the leg, or the like of the user, which is not specifically limited herein.

The multiple substances can include fat, water, blood oxygen, and the like, which is not particularly limited herein. The first set of data may include substance contents of different substances or may include a percentage of each substance, which is not limited herein.

Figure 2C:
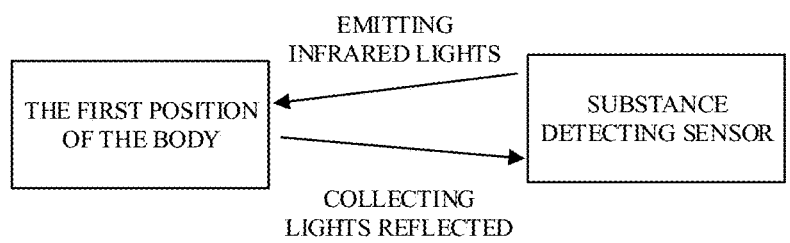
FIG. 2C is a schematic diagram of detecting substance content with a substance detecting sensor according to an implementation of the present disclosure.
Figure 2D:
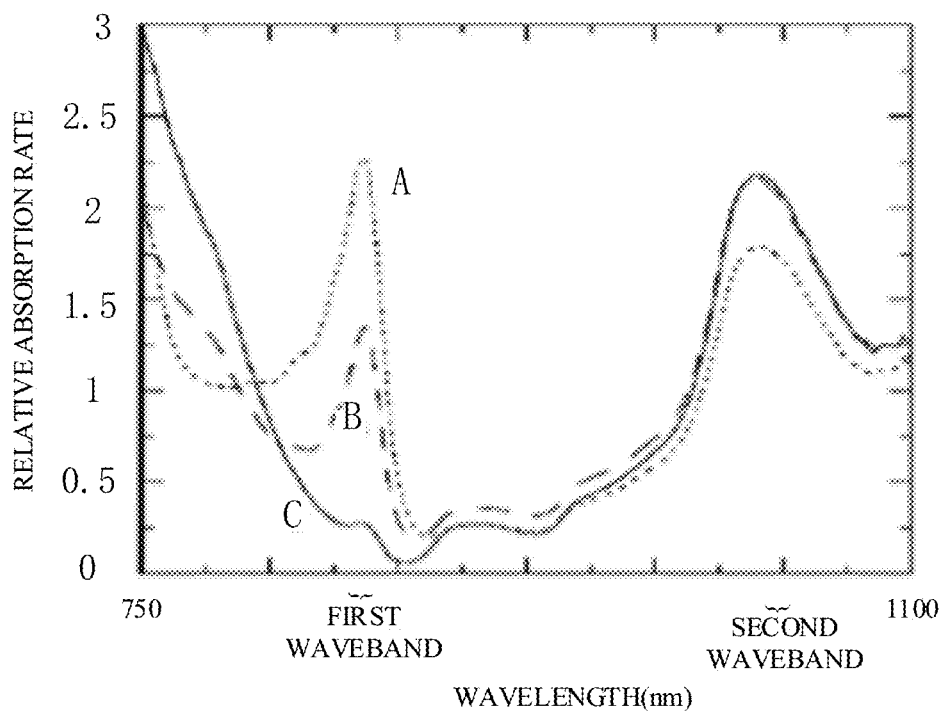
FIG. 2D is an exemplary diagram of an infrared spectrum according to an implementation of the present disclosure.

The first set of data on the multiple substances in the first position of the body of the user can be obtained by scanning the first position with the substance detecting sensor as illustrated in FIG. 2C to FIG. 2D. As illustrated in FIG. 2C, the substance detecting sensor of the electronic device scans the first position of the body of the user, emits infrared lights to the first position, and acquires infrared lights reflected back. Then an infrared spectrum, as illustrated in FIG. 2D, is drawn according to infrared lights which are reflected by substances and acquired by the substance detecting sensor. Finally, the first set of data on the first position of the body is obtained by analyzing the infrared spectrum.

The first set of data on the first position of the body can be obtained according to the infrared spectrum as follows. As illustrated in FIG. 2D, A, B, and C represent respectively infrared absorption spectrum curves obtained by scanning different body parts by the electronic device. For example, A represents an infrared absorption spectrum curve obtained by scanning the abdomen of the user, B represents an infrared absorption spectrum curve obtained by scanning the leg of the user, and C represents an infrared absorption spectrum curve obtained by scanning the arm of the user. The substance detecting sensor is integrated with N channels for different wavelengths ranging from 750 nm (nanometer) to 1100 nm. Infrared lights of different wavelengths are emitted via each channel, then an infrared spectrum illustrated in FIG. 2D is drawn according to infrared lights reflected back which are collected by each channel, and accordingly wavebands in which absorption peaks appear are determined, where the absorption peaks appearing in different wavebands represent different substances. A first mapping relationship set between substances and wavebands is stored in a database. For instance, absorption peaks of curve A, absorption peaks of curve B, and absorption peaks of curve C appear in a first waveband and at a second waveband. It can be determined, by querying the first mapping relationship set in the database, that absorption peaks appearing in the first waveband indicate that the abdomen, the leg, and the arm each have a first substance, and absorption peaks appearing in the second waveband indicate that the abdomen, the leg, and the arm each have a second substance. In addition, the absorption peaks of curve A, the absorption peaks of curve B, and the absorption peaks of curve C have different peak values at the first waveband and at the second waveband, which indicates that the abdomen, the leg, and the arm have different substance contents in terms of the first substance and the second substance. Besides, a second mapping relationship set between peak values of absorption peaks of different substances and substance contents is stored in the database. As such, multiple mapping relationships corresponding to the first substance in the second mapping relationship set are queried according to a peak value of the absorption peak of curve A, a peak value of the absorption peak of curve B, and a peak value of the absorption peak of curve C regarding the first substance, to determine a substance content in curve A, a substance content in curve B, and a substance content in curve C regarding the first substance. Similarly, multiple mapping relationships corresponding to the second substance in the second mapping relationship set are queried according to a peak value of the absorption peak of curve A, a peak value of the absorption peak of curve B, and a peak value of the absorption peak of curve C regarding the second substance, to determine a substance content in curve A, a substance content in curve B, and a substance content in curve C regarding the second substance. In this way, the first set of data on multiple first positions of the body is determined.

At 202, the electronic device determines, with the camera, a body part corresponding to the first position.

Since the substance detecting sensor is disposed near the camera, while enabling the substance detecting sensor, the electronic device can enable at the same time the camera to determine the body part corresponding to the first position. Alternatively, the camera can be enabled, through user operation, to determine the body part corresponding to the first position, which is not limited herein.

The body part corresponding to the first position can be determined as follows. As an example, the body part can be determined by feature analysis of an image of the first position, for example, the first position is determined as the abdomen if the first position has a navel. As another example, the body part can be determined according to a circumference of the first position, for example, the first position is determined as the arm if the first position has a circumference of 15 cm (centimeter) to 25 cm, or the first position is determined as a thigh if the first position has a circumference of 35 cm to 50 cm. As another example, the electronic device can determine the body part by feature comparison between an image of the first position acquired by the camera and preset images of different positions of the user, which is not particularly limited herein.

At 203, the electronic device determines and pushes a fitness plan according to the first set of data and the body part.

The manner in which the electronic device pushes the fitness plan according to the first set of data and the body part can be various. For instance, the first set of data can be sent to a cloud database. The cloud database selects, according to experience in fitness shared by multiple users, at least one fitness plan which matches the first set of data on the body part of the user and sends the selected fitness plan to the electronic device. For another instance, fitness goals to be achieved each day can be determined according to the current first set of data on the user, target data set by the user, a fitness period, or the like, where the fitness goals to be achieved each day may or may not be equal to each other, which is not limited herein. Thereafter, a user-specific fitness plan is designed according to the fitness goals to be achieved each day and fitness goals that can be achieved by the body part in terms of different exercise types, and the fitness plan is then pushed to the user, which is not limited herein.

Figure 2E:
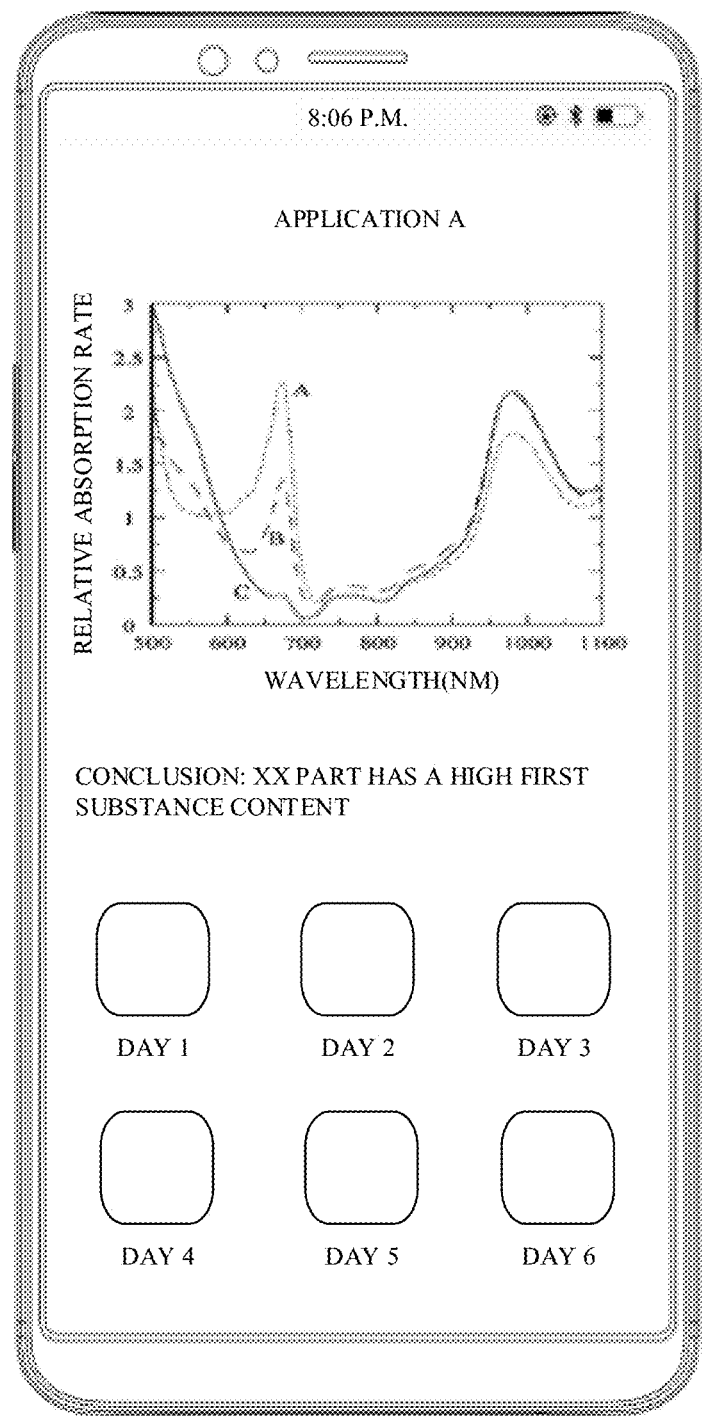
FIG. 2E is a schematic diagram of a fitness-plan pushing interface in a fitness application according to an implementation of the present disclosure.

The fitness plan can include an exercise plan, a diet plan, etc., which is not specifically limited herein. The fitness plan can be pushed in an interface of a fitness guiding application, as illustrated in FIG. 2E. A fitness plan of one fitness period can be pushed to the user according to data on substance contents of different substances in each body part detected by scanning three different body parts of the user. For example, one fitness period has six days. In this way, a fitness plan corresponding to each day can be selected (by clicking, for example) every day, which makes it more convenient for the user to carry out fitness plans.

As can be seen, in this implementation, the electronic device obtains the first set of data on the multiple substances in the first position of the body of the user by scanning the first position with the substance detecting sensor; determines, with the camera, the body part corresponding to the first position; pushes the fitness plan according to the first set of data and the body part. As such, the electronic device can determine, with the camera and the substance detecting sensor respectively, a substance content of any part of the body of the user, such that more convenient and accurate substance detection for human body can be achieved. In addition, an effective fitness plan can be designed for a specific body part according to substance composition detected, which is possible to achieve an accurate fitness guidance for the user to avoid indiscriminate fitness exercise and thus beneficial to achieving convenient and proper fitness exercise for the user.

In some implementations, the fitness plan is pushed according to the first set of data and the body part as follows. A numerical interval to which each data in the first set of data belongs is determined. Each data is scored according to the numerical interval. A total score of the first set of data is calculated according to a weight of each data in the first set of data. The fitness plan which matches the total score and the body part is acquired. The fitness plan is pushed.

In some implementations, each substance corresponds to multiple different numerical intervals and corresponds to different division manners of numerical intervals. Each numerical interval has a mapping relationship with scores. For instance, the first set of data includes a fat content and a water content, where the water content is 50% and the fat content is 27%. The 50% water content belongs to a water content interval of 40%~60%, and a score corresponding to the interval of 40%~60% is 80 according to a corresponding mapping relationship. The 27% fat content belongs to a fat content interval of 25%~30%, and a score corresponding to the interval of 25%~30% is 40 according to a corresponding mapping relationship. When a weight of the water content in the first set of data is 0.7 and a weight of the fat content in the first set of data is 0.3, the total score is 0.7*80+0.3*40, that is, 68.

The manner in which the electronic device acquires the fitness plan which matches the total score and the body part can be various. For example, a mapping relationship between body parts, total scores, and fitness plans can be stored in advance, and the fitness plan can be determined according to the mapping relationship. Alternatively, the electronic device can receive a fitness plan matching the body part that is pushed according to the total score by the cloud database, which is not particularly limited herein.

As can be seen, in this implementation, instead of pushing the fitness plan indiscriminately, the electronic device scores the body part of the user according to the numerical interval to which each data belongs, and determines the fitness plan according to the total score obtained, which improves accuracy of determining the fitness plan.

In this implementation, the fitness plan which matches the total score and the body part are acquired as follows. A target score set by the user is acquired. Fitness plans which match the body part are received from a database, where for each of the fitness plans received from the database, a difference between a score before a reference user carries out the fitness plan and the total score is smaller than a first threshold, and a difference between a score after the reference user carries out the fitness plan and the target score is smaller than a second threshold.

In some implementations, after receiving, from the database, the fitness plans which match the body part, the following can be conducted. At least one fitness plan which matches identity information of the user is selected from the fitness plans and then pushed to the user.

The identity information can include at least the following: age, gender, height, weight, occupation, location, etc., which is not specifically limited herein.

For example, the total score of current user A is 50, and the target score in a short term is 60. Accordingly, the cloud database will push reference fitness plans of multiple reference users B other than user A which match the body part, where the multiple reference users B have achieved, from scores which are approximate to the total score, scores which are approximate to the target score after carrying out the reference plans and are similar to user A, that is, the reference fitness plans are also applicable to user A.

The first threshold and the second threshold are empirical values. The empirical values can be verified by research staff of the electronic device through multiple experiments and preset in the electronic device before leaving the factory and can be, for example, 5 or 10, which is not limited herein.

The manner in which the at least one fitness plan which matches the identity information of the user is selected from the fitness plans can be various. For example, for each of the fitness plans, a match degree between the user and a user who carries out the fitness plan is determined according to the identity information, and a fitness plan of the highest match degree is determined as the at least one fitness plan. Alternatively, fitness plans carried out by users, in the multiple users, who have similarities to the user in at least four aspects regarding the identity information can be determined as the at least one fitness plan, which is not limited herein.

As can be seen, in this implementation, the electronic device acquires, through interaction with the database, fitness plans which match the user and then determines, according to the identity information of the user, the at least one fitness plan which is the most suitable for the user, thereby improving match degree and applicability of fitness guidance.

In some implementations, the fitness plan includes an exercise plan. After pushing the fitness plan according to the first set of data and the body part, the following is conducted. A heart rate and a blood oxygen level of the user are acquired, when the exercise plan is carried out by the user. The user is guided in exercise velocity according to the heart rate and the blood oxygen level.

The heart rate and the blood oxygen level of the user can be acquired with a wearable device. The blood oxygen level can also be acquired with the substance detecting sensor. The wearable device can be provided with a heart rate sensor and a blood oxygen sensor. The manner in which the user is guided in exercise velocity according to the heart rate and the blood oxygen level can be various. For example, when a change rate in heart rate and/or blood oxygen level before and after the user carries out the exercise plan is higher than a threshold, remind the user to reduce exercise velocity. Alternatively, a mapping relationship between heart rates, blood oxygen levels, and exercise velocities is preset in the electronic device, and guide the user in exercise velocity according to the mapping relationship, which is not limited herein.

As can be seen, in this implementation, after pushing the fitness plan, the electronic device monitors continuously in real time the heart rate and the blood oxygen level of the user during exercise when the exercise plan is carried out by the user and guides the user in exercise velocity according to result monitored, such that the electronic device can be more intelligent and fitness guidance can be conducted in a healthier manner.

In some implementations, the user is guided in exercise velocity according to the heart rate and the blood oxygen level as follows. A first exercise velocity of the user is acquired. A first standard interval for the heart rate and a second standard interval for the blood oxygen level are determined according to the first exercise velocity. When the heart rate is higher than a maximum value of the first standard interval and/or the blood oxygen level is lower than a minimum value of the second standard interval, a reminder message is outputted or displayed for the user, where the reminder message is used for reminding the user to reduce the first exercise velocity to a second exercise velocity.

The second exercise velocity can be determined in various manners. For instance, an exercise velocity which matches the heart rate and the blood oxygen level of the user is determined (hereinafter, "matched exercise velocity" for short), and then any exercise velocity lower than or equal to the matched exercise velocity is determined as the second exercise velocity. Alternatively, the second exercise velocity is directly set to a minimum exercise velocity, which is not particularly limited herein.

As can be seen, in this implementation, the electronic device determines, according to the current first exercise velocity of the user, whether the heart rate and the blood oxygen level are out of limits; when the heart rate is above the first standard interval and/or the blood oxygen level is below the second standard interval, reminds the user to reduce the first exercise velocity through the reminder message, which is beneficial to avoiding physical problems due to excessively high exercise velocity of the user, thereby improving intelligence of the electronic device and accuracy of fitness guidance.

In some implementations, the fitness plan further includes a diet plan. After pushing the fitness plans according to the first set of data and the body part, the following is conducted. A second set of data on food is acquired by scanning the food with the substance detecting sensor, when the diet plan is carried out by the user. The user is guided in carrying out the diet plan according to the second set of data.

The second set of data may be data on protein, carbohydrate, sugar, etc., which is not specifically limited herein.

In one implementation, when the diet plan is carried out by the user, a first calorie value of the food is detected with the substance detecting sensor. A total amount of the food is acquired with the camera or the substance detecting sensor. A first calorie value in the second set of data and a second calorie value in the diet plan are determined and compared with each other. The user is guided in carrying out the diet plan by pushing an intake of the food according to a second calorie value in the diet plan, the total amount of the food, and the first calorie value in the second set of data, when the first calorie value is detected to be higher than the second calorie value.

The intake of the food is smaller than the total amount of the food. The intake of the food is an intake allowed for the user. The electronic device can determine, according to a ratio of the first calorie to the second calorie, a ratio of the total amount of the food to the intake of the food to calculate the intake of the food according to the total amount of the food.

As can be seen, in this implementation, after pushing the fitness plan, the electronic device acquires the first calorie of the food of the user and reminds the user of the intake of the food when the diet plan is carried out by the user, which is beneficial to avoiding failure in carrying out the diet plan, thereby making the electronic device more intelligent and fitness guidance more effective.

Figure 3:
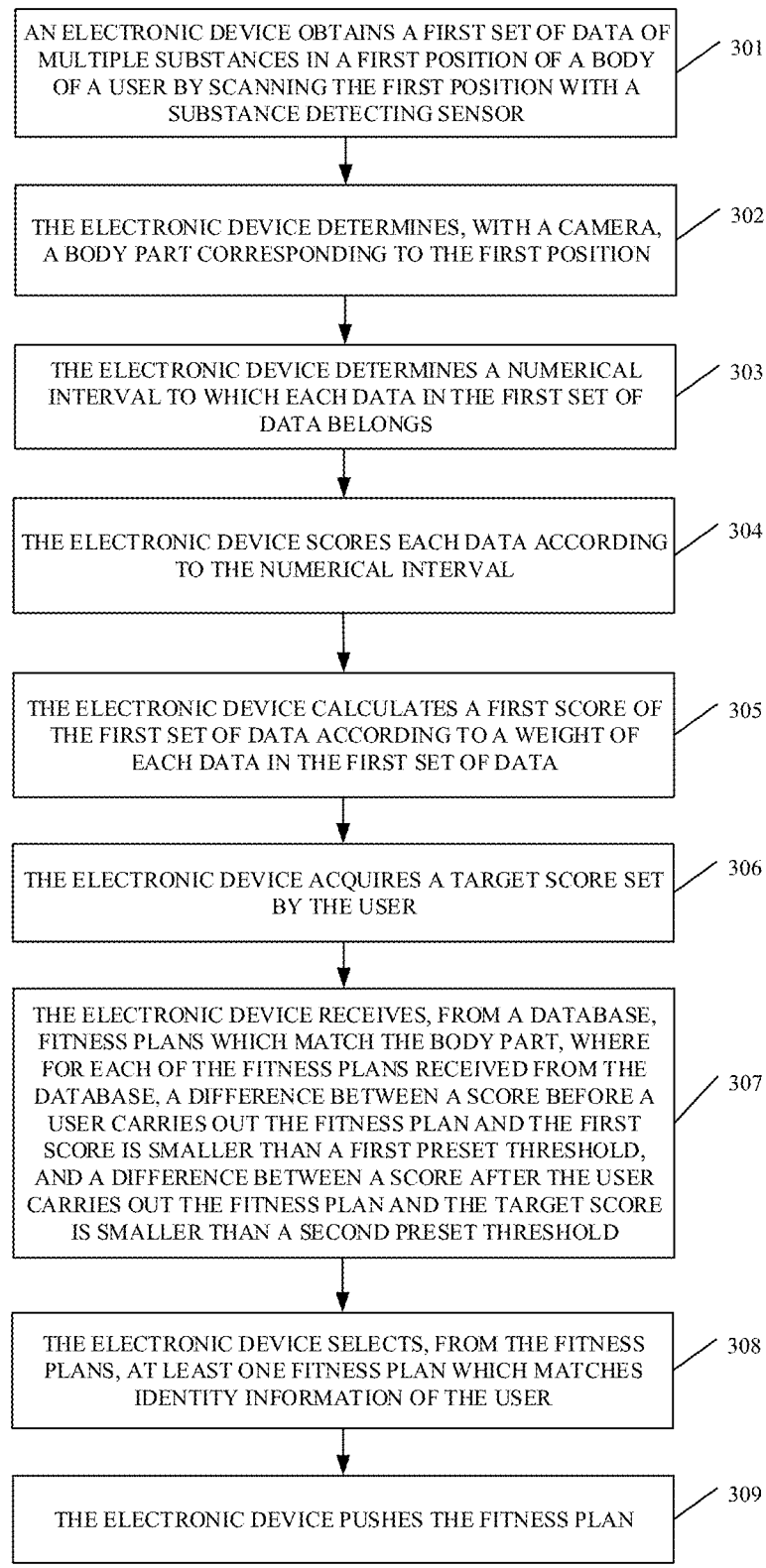
FIG. 3 is a schematic flowchart of a method for pushing information according to another implementation of the present disclosure.

Similar to implementations illustrated in FIG. 2A, FIG. 3 is a schematic flowchart of a method for pushing information according to another implementation of the present disclosure. The method is applicable to the electronic device illustrated in FIG. 1A to FIG. 1C including a substance detecting sensor and a camera. The substance detecting sensor is disposed near the camera. As illustrated in FIG. 3, the method begins at block 301.

At 301, the electronic device obtains a first set of data on multiple substances in a first position of a body of a user by scanning the first position with the substance detecting sensor.

At 302, the electronic device determines, with the camera, a body part corresponding to the first position.

At 303, the electronic device determines a numerical interval to which each data in the first set of data belongs.

At 304, the electronic device assigns a score to each data according to the numerical interval.

At 305, the electronic device calculates a total score of the first set of data according to a weight of each data in the first set of data.

At 306, the electronic device acquires a target score which is set by the user.

At 307, the electronic device receives, from a database, fitness plans which match the body part, where for each of the fitness plans received from the database, a difference between a score before a user carries out the fitness plan and the total score is smaller than a first threshold, and a difference between a score after the user carries out the fitness plan and the target score is smaller than a second threshold.

At 308, the electronic device selects, from the fitness plans, at least one fitness plan which matches identity information of the user.

At 309, the electronic device pushes the fitness plan selected.

As can be seen, in this implementation, the electronic device obtains the first set of data on the multiple substances in the first position of the body of the user by scanning the first position with the substance detecting sensor; determines, with the camera, the body part corresponding to the first position; pushes the fitness plan according to the first set of data and the body part. As such, the electronic device can determine, with the camera and the substance detecting sensor respectively, a substance content of any part of the body of the user, such that more convenient and accurate substance detection for human body can be achieved. In addition, an effective fitness plan can be designed for a specific body part according to substance composition detected, which is possible to achieve an accurate fitness guidance for the user to avoid indiscriminate fitness exercise and thus beneficial to achieving convenient and proper fitness exercise for the user.

In addition, instead of pushing the fitness plan indiscriminately, the electronic device assigns a score to the body part of the user according to the numerical interval to which each data belongs, and determines the fitness plan according to the total score obtained, which improves accuracy of determining fitness plans.

Furthermore, the electronic device acquires, through interaction with the database, fitness plans which match the user and then determines, according to the identity information of the user, the at least one fitness plan which is the most suitable for the user, thereby improving match degree and applicability of fitness guidance.

Figure 4:
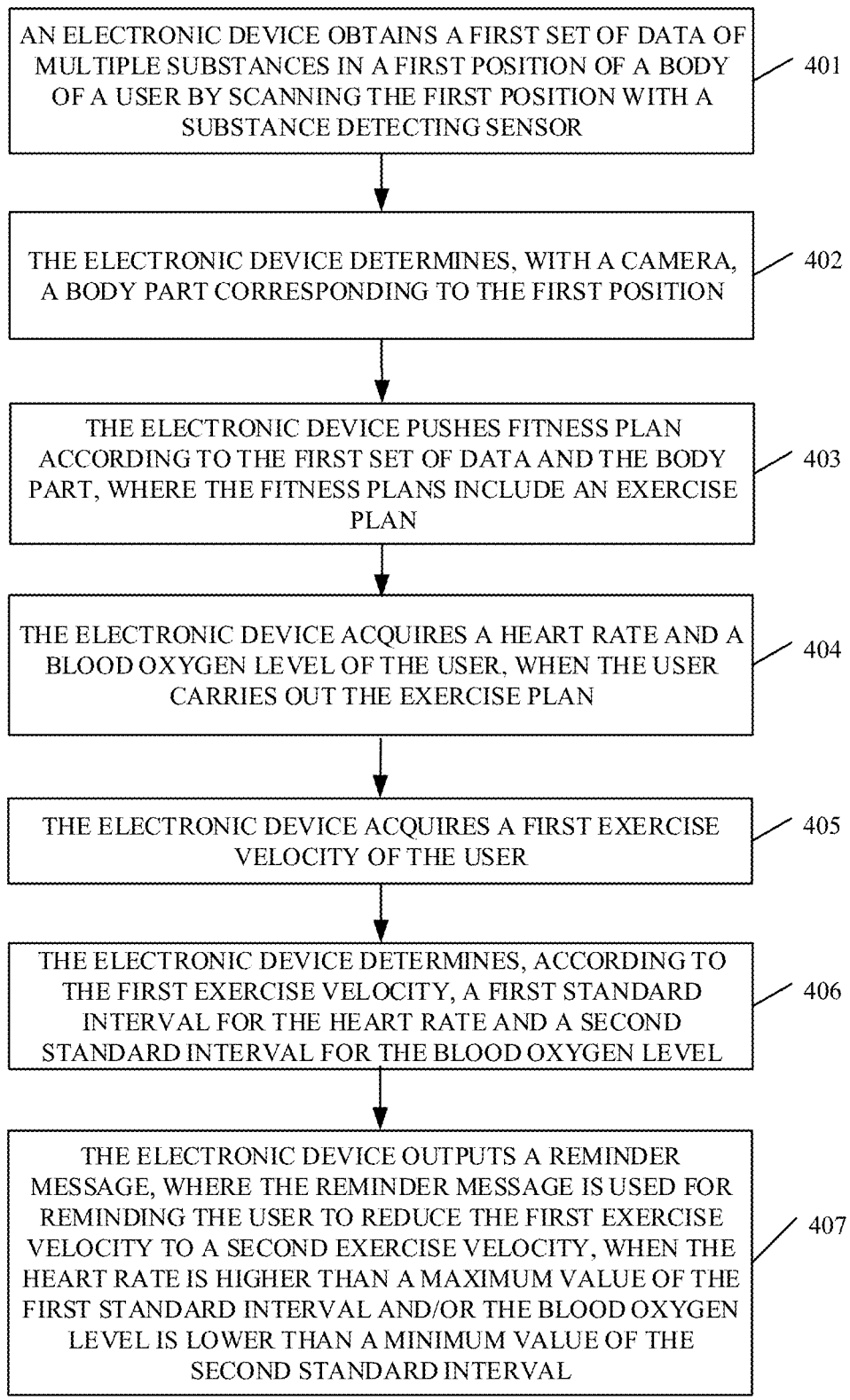
FIG. 4 is a schematic flowchart of a method for pushing information according to another implementation of the present disclosure.

Similar to implementations illustrated in FIG. 2A, FIG. 4 is a schematic flowchart of a method for pushing information according to another implementation of the present disclosure. The method is applicable to the electronic device illustrated in FIG. 1A to FIG. 1C. The substance detecting sensor and a camera. The substance detecting sensor is disposed near the camera. As illustrated in FIG. 4, the method begins at block 401.

At 401, the electronic device obtains a first set of data on multiple substances in a first position of a body of a user by scanning the first position with the substance detecting sensor.

At 402, the electronic device determines, with the camera, a body part corresponding to the first position.

At 403, the electronic device pushes a fitness plan according to the first set of data and the body part, where the fitness plan includes an exercise plan.

At 404, the electronic device acquires a heart rate and a blood oxygen level of the user, when the exercise plan is carried out by the user.

At 405, the electronic device acquires a first exercise velocity of the user.

At 406, the electronic device determines, according to the first exercise velocity, a first standard interval for the heart rate and a second standard interval for the blood oxygen level.

At 407, the electronic device outputs a reminder message, where the reminder message is used for reminding the user to reduce the first exercise velocity to a second exercise velocity, when the heart rate is higher than a maximum value of the first standard interval and/or the blood oxygen level is lower than a minimum value of the second standard interval.

As can be seen, in this implementation, the electronic device obtains the first set of data on the multiple substances in the first position of the body of the user by scanning the first position with the substance detecting sensor; determines, with the camera, the body part corresponding to the first position; pushes the fitness plan according to the first set of data and the body part. As such, the electronic device can determine, with the camera and the substance detecting sensor respectively, a substance content of any part of the body of the user, such that more convenient and accurate substance detection for human body can be achieved. In addition, an effective fitness plan can be designed for a specific body part according to substance composition detected, which is possible to achieve an accurate fitness guidance for the user to avoid indiscriminate fitness exercise and thus beneficial to achieving convenient and proper fitness exercise for the user.

In addition, after pushing the fitness plan, the electronic device monitors continuously in real time the heart rate and the blood oxygen level of the user during exercise when the exercise plan is carried out by the user and guides the user in exercise velocity according to result monitored, such that the electronic device can be more intelligent and fitness guidance can be conducted in a healthier manner.

Furthermore, the electronic device determines, according to the current first exercise velocity of the user, whether the heart rate and the blood oxygen level are out of limits; when the heart rate is beyond the first standard interval and/or the blood oxygen level is beyond the second standard interval, reminds the user to reduce the first exercise velocity through the reminder message, which is beneficial to avoiding physical problems due to excessively high exercise velocity of the user, thereby improving intelligence of the electronic device and accuracy of fitness guidance.

According to implementations of the disclosure, a computer readable storage medium is provided. The computer readable storage medium is configured to store computer programs which, when executed by a computer, are operable with the computer to: invoke a sensor to scan a first position of a body of a user to obtain a first set of data on a plurality of body substances in the first position, wherein the first set of data comprises at least one of: contents of each body substance, and percentage of each body substance; invoke a camera to capture a picture of the first position; invoke a processor to determine a body part corresponding to the first position by feature analysis of the picture, and invoke the processor to determine a fitness plan according to the first set of data and the body part and push, via the display, the fitness plan determined.

The computer readable storage medium is further configured to store computer programs which, when executed by a computer, are operable with the computer to: emit infrared lights to the first position; receive infrared lights reflected by the first position; determine the first set of data according to infrared spectrums of the infrared lights reflected.

Figure 5:
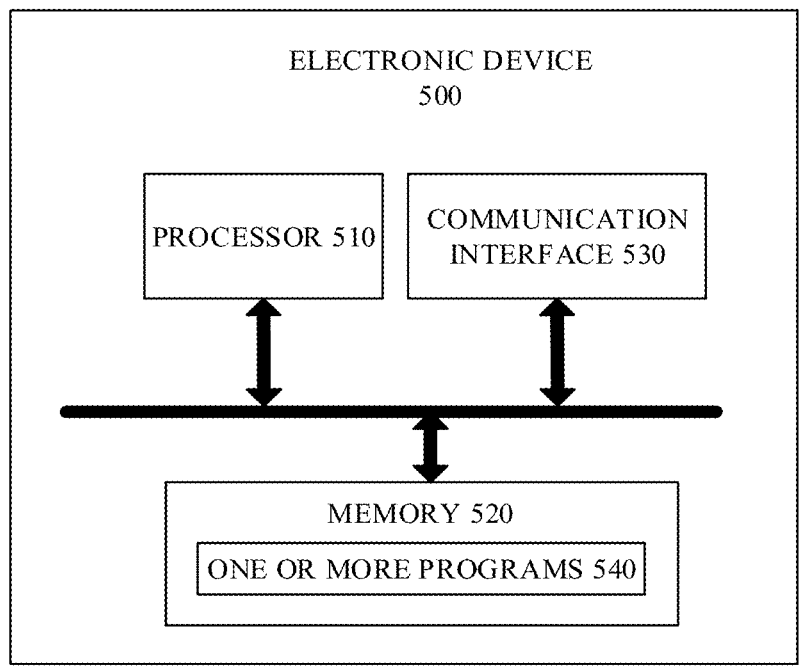
FIG. 5 is a schematic structural diagram of an electronic device according to an implementation of the present disclosure.

Similar to implementations illustrated in FIG. 2A, FIG. 3, and FIG. 4, FIG. 5 is a schematic structural diagram of an electronic device 500 according to another implementation of the present disclosure. The electronic device 500 includes a substance detecting sensor and a camera. The substance detecting sensor is disposed near the camera. As illustrated in FIG. 5, the electronic device 500 includes a processor 510, a memory 520, a communication interface 530, and one or more programs 540 stored in the memory and configured to be executed by the processor. The one or more programs 540 include instructions operable with the processor to: obtain a first set of data on multiple substances in a first position of a body of a user by scanning the first position with the substance detecting sensor; determine, with the camera, a body part corresponding to the first position; push a fitness plan according to the first set of data and the body part.

As can be seen, in this implementation, the electronic device obtains the first set of data on the multiple substances in the first position of the body of the user by scanning the first position with the substance detecting sensor; determines, with the camera, the body part corresponding to the first position; pushes the fitness plan according to the first set of data and the body part. As such, the electronic device can determine, with the camera and the substance detecting sensor respectively, a substance content of any part of the body of the user, such that more convenient and accurate substance detection for human body can be achieved. In addition, an effective fitness plan can be designed for a specific body part according to substance composition detected, which is possible to achieve an accurate fitness guidance for the user to avoid indiscriminate fitness exercise and thus beneficial to achieving convenient and proper fitness exercise for the user.

In some implementations, in terms of pushing the fitness plan according to the first set of data and the body part, the one or more programs 540 include instructions operable with the processor to: determine a numerical interval to which each data in the first set of data belongs; assign a score to each data according to the numerical interval; calculate a total score of the first set of data according to a weight of each data in the first set of data; acquire the fitness plan which matches the total score and the body part; push the fitness plan.

In some implementations, in terms of acquiring the fitness plan which matches the total score and the body part, the one or more programs 540 include instructions operable with the processor to: acquire a target score set by the user; receive, from a database, fitness plans which match the body part, where for each of the fitness plans received from the database, a difference between a score before a user carries out the fitness plan and the total score is smaller than a first threshold, and a difference between a score after the user carries out the fitness plan and the target score is smaller than a second threshold.

In some implementations, after receiving, from the database, the fitness plans which match the body part, the one or more programs 540 further include instructions operable with the processor to: select, from the fitness plans, at least one fitness plan which matches identity information of the user.

In some implementations, the fitness plan includes an exercise plan. After pushing the fitness plan according to the first set of data and the body part, the one or more programs 540 further include instructions operable with the processor to: when the exercise plan is carried out by the user, acquire a heart rate and a blood oxygen level of the user; guide the user in exercise velocity according to the heart rate and the blood oxygen level.

In some implementations, in terms of guiding the user in exercise velocity according to the heart rate and the blood oxygen level, the one or more programs 540 include instructions operable with the processor to: acquire a first exercise velocity of the user; determine, according to the first exercise velocity, a first standard interval for the heart rate and a second standard interval for the blood oxygen level; output a reminder message, when the heart rate is higher than a maximum value of the first standard interval and/or the blood oxygen level is lower than a minimum value of the second standard interval, where the reminder message is used for reminding the user to reduce the first exercise velocity to a second exercise velocity.

In some implementations, the fitness plan further includes a diet plan. After pushing the fitness plan according to the first set of data and the body part, the one or more programs 540 further include instructions operable with the processor to: acquire a second set of data on food by scanning the food with the substance detecting sensor; guide the user in carrying out the diet plan according to the second set of data.

In some implementations, in terms of guiding the user in carrying out the diet plan according to the second set of data, the one or more programs 540 include instructions operable with the processor to: acquire, with the camera, a total amount of the food; guide the user in carrying out the diet plan by pushing an intake of the food according to a second calorie in the diet plan, the total amount of the food, and a first calorie in the second set of data, when the first calorie is detected to be higher than the second calorie.

The foregoing technical solutions of implementations of the disclosure are mainly described from a perspective of execution of the method. It can be understood that, in order to implement the above functions, the electronic device includes hardware structures and/or software modules for performing respective functions. Those of ordinary skill in the art will appreciate that units and algorithmic operations of various examples described in connection with implementations herein can be implemented in hardware or a combination of computer software and hardware. Whether these functions are implemented by means of hardware or software depends on the particular application and the design constraints of the associated technical solution. For a specific application, those skilled in the art may use different methods to implement the described functionality, but such implementation should not be regarded as beyond the scope of the disclosure.

In implementations of the present disclosure, the electronic device can be divided into different functional units according to the above method implementations. For example, the electronic device can be divided into different functional units corresponding to each function, or two or more functions may be integrated into one processing unit. The integrated unit can take the form of hardware or a software functional unit. It is to be noted that, division of units provided herein is illustrative and is just a logical function division. In practice, there can be other manners of division.

Figure 6:
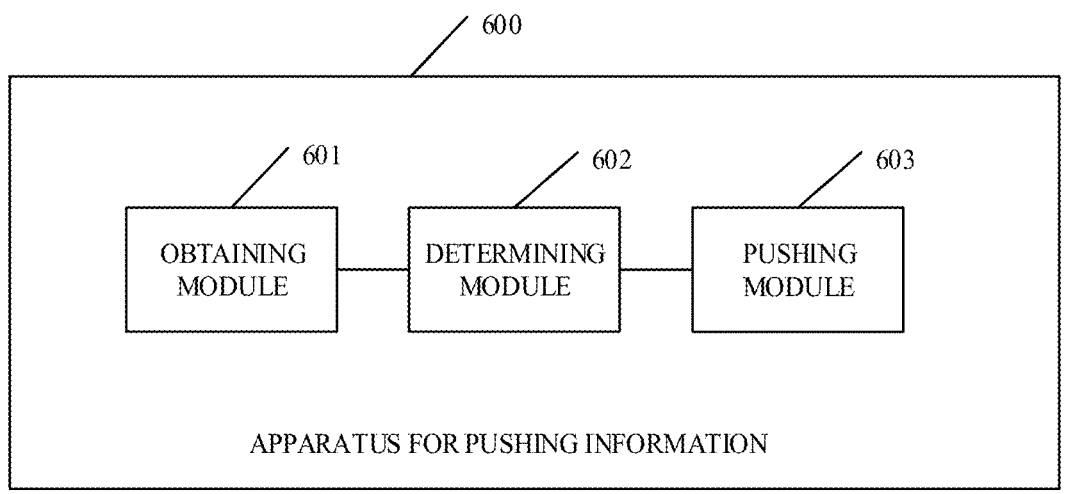
FIG. 6 is a structural block diagram illustrating functional modules of an apparatus for pushing information according to an implementation of the present disclosure.

FIG. 6 is a structural block diagram illustrating functional modules of an apparatus 600 for pushing information according to an implementation of the present disclosure. The apparatus 600 is applicable to an electronic device including a substance detecting sensor and a camera. The substance detecting sensor is disposed near the camera. The apparatus 600 includes an obtaining module 601, a determining module 602, and a pushing module 603. The obtaining module 601 is configured to obtain a first set of data on multiple substances in a first position of a body of a user by scanning the first position with the substance detecting sensor. The determining module 602 is configured to determine, with the camera, a body part corresponding to the first position. The pushing module 603 configured to push a fitness plan according to the first set of data and the body part.

As can be seen, in this implementation, the electronic device obtains the first set of data on the multiple substances in the first position of the body of the user by scanning the first position with the substance detecting sensor; determines, with the camera, the body part corresponding to the first position; pushes the fitness plan according to the first set of data and the body part. As such, the electronic device can determine, with the camera and the substance detecting sensor respectively, a substance content of any part of the body of the user, such that more convenient and accurate substance detection for human body can be achieved. In addition, an effective fitness plan can be designed for a specific body part according to substance composition detected, which is possible to achieve an accurate fitness guidance for the user to avoid indiscriminate fitness exercise and thus beneficial to achieving convenient and proper fitness exercise for the user.

In some implementations, in terms of pushing the fitness plan according to the first set of data and the body part, the pushing module 603 is configured to: determine a numerical interval to which each data in the first set of data belongs; assign a score to each data according to the numerical interval; calculate a total score of the first set of data according to a weight of each data in the first set of data; acquire the fitness plan which matches the total score and the body part; push the fitness plan.

In some implementations, in terms of acquiring the fitness plan which matches the total score and the body part, the pushing module 603 is configured to: acquire a target score which is set by the user; receive, from a database, fitness plans which match the body part, where for each of the fitness plans received from the database, a difference between a score before a user carries out the fitness plan and the total score is smaller than a first threshold, and a difference between a score after the user carries out the fitness plan and the target score is smaller than a second threshold.

In some implementations, the pushing module 603 is further configured to: select, from the fitness plans which match the body part, at least one fitness plan which matches identity information of the user.

In some implementations, the fitness plan includes an exercise plan. After pushing the fitness plan according to the first set of data and the body part, the obtaining module 601 is further configured to acquire a heart rate and a blood oxygen level of the user, when the exercise plan is carried out by the user. The pushing module 603 is further configured to guide the user in exercise velocity according to the heart rate and the blood oxygen level.

In some implementations, in terms of guiding the user in exercise velocity according to the heart rate and the blood oxygen level, the pushing module 603 is configured to: acquire a first exercise velocity of the user; determine, according to the first exercise velocity, a first standard interval for the heart rate and a second standard interval for the blood oxygen level; output a reminder message, when the heart rate is higher than a maximum value of the first standard interval and/or the blood oxygen level is lower than a minimum value of the second standard interval, where the reminder message is used for reminding the user to reduce the first exercise velocity to a second exercise velocity.

In some implementations, the fitness plan further includes a diet plan. After pushing the fitness plan according to the first set of data and the body part, the obtaining module 601 is further configured to: acquire a second set of data on food by scanning the food with the substance detecting sensor, when the diet plan is carried out by the user; guide the user in carrying out the diet plan according to the second set of data.

In some implementations, in terms of guiding the user in carrying out the diet plan according to the second set of data, the obtaining module 601 is configured to acquire, with the camera, a total amount of the food. The pushing module 603 is further configured to guide the user in carrying out the diet plan by pushing an intake of the food according to a second calorie in the diet plan, the total amount of the food, and a first calorie in the second set of data, when the first calorie is detected to be higher than the second calorie.

The obtaining module 601 may be the substance detecting sensor, a wearable device, a motion sensor, or the like. The determining module 602 may be the camera. The pushing module 603 may be a communication interface or a transceiver, or may be a processor.

According to implementations of the disclosure, a computer storage medium is further provided. The computer storage medium is configured to store computer programs for electronic data interchange. The computer programs are operable with a computer to perform all or part of the operations of any of the methods described in the foregoing method implementations.

According to implementations of the present disclosure, a computer program product is further provided. The computer program product includes a non-transitory computer readable storage medium configured to store computer programs. The computer programs are operable with a computer to perform all or part of the operations of any of the methods described in the foregoing method implementations. The computer program product may be a software installation package.

It is to be noted that, for the sake of simplicity, the foregoing method implementations are described as a series of action combinations. However, it will be appreciated by those skilled in the art that the present disclosure is not limited by the sequence of actions described. The reason is that, according to the present disclosure, certain steps or operations may be executed in other orders or simultaneously. Besides, it will be appreciated by those skilled in the art that the implementations described in the specification are exemplary implementations and the actions and modules involved are not necessarily essential to the present disclosure.

In the foregoing implementations, the description of each implementation has its own emphasis. For the parts not described in detail in one implementation, reference may be made to related descriptions in other implementations.

In implementations of the disclosure, the apparatus disclosed in implementations provided herein may be implemented in other manners. For example, the device/apparatus implementations described above are merely illustrative; for instance, the division of the unit is only a logical function division and there can be other manners of division during actual implementations, for example, multiple units or assemblies may be combined or may be integrated into another system, or some features may be ignored or skipped. In addition, coupling or communication connection between each illustrated or discussed component may be direct coupling or communication connection, or may be indirect coupling or communication among devices or units via some interfaces, and may be electrical connection, or other forms of connection.

The units described as separate components may or may not be physically separated, the components illustrated as units may or may not be physical units, that is, they may be in the same place or may be distributed to multiple network elements. All or part of the units may be selected according to actual needs to achieve the purpose of the technical solutions of the implementations.

In addition, the functional units in various implementations of the present disclosure may be integrated into one processing unit, or each unit may be physically present, or two or more units may be integrated into one unit. The above-mentioned integrated unit can be implemented in the form of hardware or a software function unit.

The integrated unit may be stored in a computer-readable memory when it is implemented in the form of a software function unit and is sold or used as a separate product. Based on such understanding, the technical solutions of the present disclosure essentially, or the part of the technical solutions that contribute to the related art, or all or part of the technical solutions, may be embodied in the form of a software product which is stored in a memory and includes instructions for causing a computer device (which may be a personal computer, a server, or a network device, and so on) to perform all or part of the steps described in the various implementations of the present disclosure. The memory includes various medium capable of storing program codes, such as a universal serial bus (USB) flash disk, a read-only memory (ROM), a RAM, a removable hard disk, a magnetic disk, a compact disc (CD), or the like.

It will be understood by those of ordinary skill in the art that all or part of the steps of the various methods of the implementations described above may be accomplished by means of a program to instruct associated hardware, and the program may be stored in a computer-readable memory, which may include a flash memory, a ROM, a RAM, a magnetic disk, or a CD, and so on.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. An electronic device comprising:
a substance detecting sensor configured to obtain a first set of data on a plurality of substances in a first position of a body of a user by scanning the first position;

a camera configured to determine a body part corresponding to the first position;

a display; and a processor coupled with the substance detecting sensor, the camera, and the display and configured to determine a fitness plan according to the first set of data and the body part, and push the fitness plan determined via the display;

wherein the processor is configured to determine the fitness plan according to the first set of data and the body part is configured to:

for each data in the first set of data, determine, a numerical interval to which the data belongs; and assign a score to each data according to the numerical interval;

calculate a total score of the first set of data according to the score and a weight of each data in the first set of data; and determine a fitness plan which matches the total score and the body part as the fitness plan to be pushed.

2. The electronic device of claim 1, wherein the processor configured to determine the fitness plan which matches the total score and the body part is configured to:

acquire a target score which is set in advance; and receive, from a database, fitness plans which match the body part, wherein for each of the fitness plans received from the database, a difference between a score before a reference user carries out the fitness plan and the total score is smaller than a first threshold, and a difference between a score after the reference user carries out the fitness plan and the target score is smaller than a second threshold.

3. The electronic device of claim 2, wherein the processor is further configured to:

select, from the fitness plans which match the body part, at least one fitness plan which matches identity information of the user as the fitness plan to be pushed.

4. The electronic device of claim 1, wherein the fitness plan comprises an exercise plan, and the processor is further configured to:

acquire a heart rate and a blood oxygen level of the user when the exercise plan is carried out by the user; and guide the user in exercise velocity according to the heart rate and the blood oxygen level.

5. The electronic device of claim 4 further comprising a velocity sensor, wherein the processor configured to guide the user in exercise velocity according to the heart rate and the blood oxygen level is configured to:

acquire, with the velocity sensor, a first exercise velocity of the user;

determine, according to the first exercise velocity, a first standard interval for the heart rate and a second standard interval for the blood oxygen level; and output a reminder message via the display when at least one of the following is satisfied:

the heart rate is higher than a maximum value of the first standard interval; and the blood oxygen level is lower than a minimum value of the second standard interval;

wherein the reminder message is used for reminding the user to reduce the first exercise velocity to a second exercise velocity.

6. The electronic device of claim 1, wherein the fitness plan further comprises a diet plan, the substance detecting sensor is further configured to:

acquire a second set of data on food by scanning the food when the diet plan is carried out by the user, wherein the second set of data comprises at least one of: contents of ingredients in the food, and percentage of ingredients in the food; and the processor is configured to:

guide the user in carrying out the diet plan according to the second set of data.

7. The electronic device of claim 6, wherein the substance detecting sensor is configured to:

determine a total amount of the food by scanning the food;

the processor configured to guide the user in carrying out the diet plan according to the second set of data is configured to:

determine a first calorie value in the second set of data and determine a second calorie value in the diet plan;

compare the first calorie value with the second calorie value; and guide the user in carrying out the diet plan by pushing an intake of the food according to the second calorie value, the total amount of the food, and the first calorie value, when the first calorie value is higher than the second calorie value.

8. The electronic device of claim 1, wherein the camera is embodied as two cameras, the substance detecting sensor is disposed between the two cameras.

9. The electronic device of claim 1, wherein the substance detecting sensor is disposed adjacent to the camera.

10. A method for pushing information, being applicable to an electronic device comprising a substance detecting sensor, a camera, and a display, the method comprising:

obtaining a first set of data on a plurality of substances in a first position of a body of a user by scanning the first position with the substance detecting sensor;

determining, with the camera, a body part corresponding to the first position; and determining a fitness plan according to the first set of data and the body part and pushing the fitness plan determined via the display;

wherein determining the fitness plan according to the first set of data and the body part comprises:

for each data in the first set of data:

determining a numerical interval to which the data belongs; and assigning a score to the data according to the numerical interval;

calculating a total score of the first set of data according to the score and a weight of each data in the first set of data; and determining the fitness plan which matches the total score and the body part.

11. The method of claim 10, wherein determining the fitness plan which matches the total score and the body part comprises:

acquiring a target score which is set in advance; and receiving, from a database, fitness plans which match the body part, wherein for each of the fitness plans received from the database, a difference between a score before a reference user carries out the fitness plan and the total score is smaller than a first threshold, and a difference between a score after the reference user carries out the fitness plan and the target score is smaller than a second threshold.

12. The method of claim 11, further comprising the following after receiving, from the database, the fitness plans which match the body part:

selecting, from the fitness plans, at least one fitness plan which matches identity information of the user as the fitness plan to be pushed.

13. The method of claim 10, wherein the fitness plan comprises an exercise plan and the method further comprises:
acquiring a heart rate and a blood oxygen level of the user, when the exercise plan is carried out by the user; and
guiding the user in exercise velocity according to the heart rate and the blood oxygen level.

14. The method of claim 13, wherein guiding the user in exercise velocity according to the heart rate and the blood oxygen level comprises:
acquiring a first exercise velocity of the user;
determining, according to the first exercise velocity, a first standard interval for the heart rate and a second standard interval for the blood oxygen level; and
outputting a reminder message when at least one of the following is satisfied:
the heart rate is higher than a maximum value of the first standard interval; and
the blood oxygen level is lower than a minimum value of the second standard interval;
wherein the reminder message is used for reminding the user to reduce the first exercise velocity to a second exercise velocity.

15. The method of claim 10, wherein the fitness plan further comprises a diet plan, and the method further comprises:
acquiring a second set of data on food by scanning the food with the substance detecting sensor, when the diet plan is carried out by the user; and
guiding the user in carrying out the diet plan according to the second set of data.

16. The method of claim 15, wherein guiding the user in carrying out the diet plan according to the second set of data comprises:
acquiring, with the camera, a total amount of the food;
determining a first calorie value in the second set of data and a second calorie value in the diet plan and comparing the first calorie value with the second calorie value; and
guiding the user in carrying out the diet plan by pushing an intake of the food according to the second calorie value, the total amount of the food, and the first calorie value, when the first calorie value is detected to be higher than the second calorie.

17. A non-transitory computer readable storage medium configured to store computer programs which, when executed by a computer, are operable with the computer to:
invoke a sensor to scan a first position of a body of a user to obtain a first set of data on a plurality of body substances in the first position, wherein the first set of data comprises at least one of: contents of each body substance, and percentage of each body sub stance;
invoke a camera to capture a picture of the first position;
invoke a processor to determine a body part corresponding to the first position by feature analysis of the picture; and
invoke the processor to determine a fitness plan according to the first set of data and the body part and push, via the display, the fitness plan determined;
wherein the computer programs which are operable with the computer to invoke the processor to determine the fitness plan according to the first set of data and the body part are operable with the computer to invoke the processor to:
for each data in the first set of data,
determine, a numerical interval to which the data belongs; and
assign a score to each data according to the numerical interval;
calculate a total score of the first set of data according to the score and a weight of each data in the first set of data; and
determine a fitness plan which matches the total score and the body part as the fitness plan to be pushed.

18. The non-transitory computer readable storage medium of claim 17, wherein the non-transitory computer readable storage medium is further configured to store computer programs which, when executed by a computer, are operable with the computer to:
emit infrared lights to the first position;
receive infrared lights reflected by the first position; and
determine the first set of data according to infrared spectrums of the infrared lights reflected.

* * * * *